US012758517B2

(12) United States Patent
Waisbourd-Zinman

(10) Patent No.: US 12,758,517 B2
(45) Date of Patent: Oct. 13, 2026

(54) METHODS FOR TREATMENT OF DAMAGED BILIARY DUCT

(71) Applicant: Mor Research Applications Ltd., Ramat Gan (IL)

(72) Inventor: Orith Waisbourd-Zinman, Herzelia (IL)

(73) Assignee: MOR RESEARCH APPLICATIONS LTD., Ramat Gan (IL)

(*) Notice: Subject to any disclaimer, the term of this patent is extended or adjusted under 35 U.S.C. 154(b) by 1115 days.

(21) Appl. No.: 17/758,422

(22) PCT Filed: Jan. 6, 2021

(86) PCT No.: PCT/IB2021/050058
§ 371 (c)(1),
(2) Date: Jul. 6, 2022

(87) PCT Pub. No.: WO2021/140443
PCT Pub. Date: Jul. 15, 2021

(65) Prior Publication Data
US 2023/0023026 A1 Jan. 26, 2023

Related U.S. Application Data

(60) Provisional application No. 62/957,477, filed on Jan. 6, 2020.

(51) Int. Cl.
*A61K 31/198* (2006.01)
*A61K 31/26* (2006.01)
(Continued)

(52) U.S. Cl.
CPC ............ *A61K 31/198* (2013.01); *A61K 31/26* (2013.01); *A61K 31/385* (2013.01);
(Continued)

(58) Field of Classification Search
CPC ........................................ A61K 31/198
See application file for complete search history.

(56) References Cited

U.S. PATENT DOCUMENTS

| | | | |
|---|---|---|---|
| 5,244,913 | A | 9/1993 | Coulter et al. |
| 10,028,918 | B2 | 7/2018 | Nacharaju et al. |

(Continued)

FOREIGN PATENT DOCUMENTS

| | | | |
|---|---|---|---|
| EP | 0639375 | A1 | 2/1995 |
| WO | 9312774 | A1 | 7/1993 |

(Continued)

OTHER PUBLICATIONS

Sandhir et al (N-acetyl-l-cysteine Prevents Bile Duct Ligation Induced Renal Injury by Modulating Oxidative Stress), Ind J Clin Biochem 32, 411â419 (2017)). (Year: 2017).*

(Continued)

*Primary Examiner* — Benjamin J Packard
(74) *Attorney, Agent, or Firm* — FISHERBROYLES, LLP; Roger L. Browdy

(57) ABSTRACT

Methods of treating damaged bile ducts by way of elevating glutathione (GSH) levels, restoring normal GSH levels, and/or maintaining normal GSH levels in the biliary ducts are disclosed. A disclosed method comprises local treatment of damaged biliary ducts, e.g., by directly delivering to the bile ducts lumen of at least one active agent that promotes increasing of GSH production or inhibiting of GSH degradation in the biliary epithelial cells.

20 Claims, 3 Drawing Sheets

(51) Int. Cl.
*A61K 31/385* (2006.01)
*A61K 31/593* (2006.01)
*A61K 31/7076* (2006.01)
*A61P 1/16* (2006.01)

(52) U.S. Cl.
CPC ........ *A61K 31/593* (2013.01); *A61K 31/7076* (2013.01); *A61P 1/16* (2018.01)

(56) References Cited

U.S. PATENT DOCUMENTS

| | | | | |
|---|---|---|---|---|
| 2014/0275257 | A1 * | 9/2014 | Perl | A61K 45/06 514/562 |
| 2018/0110885 | A1 | 4/2018 | Husain | |
| 2018/0200192 | A1 | 7/2018 | Gammans | |
| 2019/0038616 | A1 | 2/2019 | Puyo et al. | |
| 2019/0046487 | A1 | 2/2019 | Comb et al. | |
| 2019/0060239 | A1 | 2/2019 | Malakhov et al. | |

FOREIGN PATENT DOCUMENTS

| | | | |
|---|---|---|---|
| WO | 2019046834 | A1 | 3/2019 |
| WO | 2019084117 | A1 | 5/2019 |

OTHER PUBLICATIONS

Kakaei F., et al., "Effect of N-acetylcysteine on Liver and Kidney Function Tests After Surgical Bypass in Obstructive Jaundice: a Randomized Controlled Trial," Asian Journal of Surgery, May 28, 2019, pp. 01-08.

Waldthaler A., et al., "Continuous Intrabiliary Acetylcysteine Infusion Allowed Perioperative Chemotherapy in a Jaundiced Patient with Malignantly Transformed IPMN and Pancreatobiliary Fistula," Gastroenterology & Hepatology international Journal, Jul. 15, 2017, vol. 2(2), 03 pages.

International Search Report for Application No. PCT/IB2021/050058, mailed on May 27, 2021, 3 pages.

Lee D., "Drug-Eluting Stent in Malignant Biliary Obstruction," Journal of Hepato-Biliary-Pancreatic Surgery, Jun. 24, 2009, vol. 16(5), pp. 628-632.

Machan L., "Clinical Experience and Applications of Drug-Eluting Stents in the Noncoronary Vasculature, Bile Duct and Esophagus," Advanced Drug Delivery Reviews, Jun. 3, 2006, vol. 58(3), pp. 447-462.

MOR Research., "NAC Biliary Drug-Eluting Stent," Jul. 20, 2020, Retrieved on May 25, 2021, Retrieved from the Internet [URL: https://www.mor-research.com/technology/nac-biliary-drug-eluting-stent/].

Rezaei A., et al., "The Effects of N-Acetylcysteine on the Expression of Matrix Metalloproteinase-2 and Tissue Inhibitor of Matrix Metalloproteinase-2 in Hepatic Fibrosis in Bile Duct Ligated Rats," Hepatology Research, Oct. 30, 2008, vol. 38(12), pp. 1252-1263.

Tang Y., et al., "S-Adenosylmethionine Attenuates Bile Duct Early Warm Ischemia Reperfusion Injury After Rat Liver Transplantation," Molecular Immunology, Mar. 1, 2008, vol. 95, pp. 83-90.

Yang Y. Y., et al., "Effects of N-Acetylcysteine Administration in Hepatic Microcirculation of Rats With Biliary Cirrhosis," Journal of Hepatology, Jul. 1, 2008, vol. 49(1), pp. 25-33.

* cited by examiner

METHODS FOR TREATMENT OF DAMAGED BILIARY DUCT

FIELD OF THE INVENTION

The present disclosure relates to treatment of damaged biliary ducts by means of restoring normal glutathione GSH levels, particularly, but not exclusively, by local administration of agents that promote GSH production or prevent GSH degradation in the biliary epithelial cells (BECs).

BACKGROUND

The bile ducts carry bile from the liver and gallbladder to the small intestine. Bile is a green to yellow-brown fluid needed for proper digestion, fats absorbance and clearing of waste from the liver. Biliary ducts diseases, generally referred to as cholangiopathies, are often cureless diseases, particularly cholangitis, and may eventually necessitate liver transplantation. Cholangitis is characterized as inflammation (swelling and redness) in the bile ducts. When the bile ducts get inflamed or blocked, bile can back up into the liver, leading to liver damage and other systemic problems. The main forms of cholangiopathies include primary biliary cholangitis (PBC), primary sclerosing cholangitis (PSC), secondary cholangitis and immune cholangitis. Some types of cholangitis are mild. Other kinds can be serious and life-threatening.

Biliary stents may be used, for example, in PSC, for patients with a dominant extrahepatic biliary stricture in order to temporarily enable bile flow from the liver to the intestine, but this treatment does not cure the disease.

N-acetylcysteine (NAC) is a precursor of glutathione and acts as a direct scavenging agent. In addition to its antioxidant effects, NAC exerts anti-inflammatory effects. NAC is known to exert protective effects in liver and kidney injury, for example, treatment with NAC for prevention of bile duct ligation-induced renal injury is known.

SUMMARY

Damage in the biliary system might lead to blockage of the bile ducts that might result in serious pathological consequences. Blockage of bile ducts may be facilitated by any of the various cholangiopathies and/or cholestasis known, such as postoperative complications, ischemic insults, gallstones, tumors of the bile ducts and liver diseases such as primary biliary cirrhosis (PBC) and primary sclerosing cholangitis (PSC). For example, ischemic damage to the biliary tree is a serious complication in liver transplantations. Biliary obstruction might need endoscopic, radiologic and/or surgical intervention to maintain biliary drainage, for example, a surgical bypass. However, endoscopic and radiologic drainages of biliary system, as well as surgical interventions, are not feasible in all patients. When biliary drainage or reconstruction is not possible or has failed, liver transplantation is currently the only potential cure.

The present disclosure relates to methods of treating damaged bile ducts and/or preventing or inhibiting damage in the bile ducts of a subject, by way of elevating glutathione (GSH) levels, restoring normal GSH levels, and/or maintaining normal GSH levels in the biliary ducts of the subject. A disclose method comprises at least the step of administering to the subject a pharmaceutically effective amount of one or more active agents which promote at least one of: increasing GSH production or inhibiting GSH degradation in the biliary epithelial cells (BECs), thereby treating damaged bile ducts and/or preventing or inhibiting damage in the bile ducts of the subject.

Some embodiments of a disclosed method pertain to the local administration, namely, directly to the bile ducts themselves and/or at the biliary ducts site, of a pharmaceutically effective amount of at least one active agent which promotes at least one of: elevation of GSH levels, restoration of normal GSH levels, or maintenance of normal GSH levels. For example, local administration may comprise directly contacting the bile ducts lumen with the active agent. The active agent may be immediately released locally at the biliary duct tree, and/or may it be released over a desired period of time, e.g., days, weeks or months, by means that provide local sustained release thereof.

Active agents which may be useful for the purpose of a disclosed method include, for example, N-acetyl-L-cysteine (L-NAC), a NAC derivative, alpha lipoic acid, calcitriol, S-adenosylmethionine (SAMe) or sulforaphane.

In some embodiment, the active agent is L-NAC, a building block of GSH, useful in increasing, restoring and/or maintain normal GSH levels in cells.

Biliary ducts treatable by a disclosed method include extrahepatic bile ducts (EHBDs) as well as intrahepatic bile ducts (IHBDs) that are damaged by, e.g., a cholangiopathy such as, but not limited to, immune-mediated cholangiopathy, infectious cholangiopathy, genetic cholangiopathy, ischemic cholangiopathy, or drug- or toxin-induced cholangiopathy. In some embodiments, biliary ducts damaged or injured by a cholangiopathy such as primary biliary cholangitis (PBC), primary sclerosing cholangitis (PSC), IgG4-related sclerosing cholangitis or biliary atresia (BA) are treated by a disclosed method.

A disclosed method is suitable for treating, preventing or inhibiting biliary ducts damage or injury due to cholestasis, namely, a decrease in bile flow, or obstruction of bile flow through intra- or extrahepatic bile ducts, caused by at least one of: a cholangiopathy, cholangitis, viral, bacterial, and/or parasitic infections, oxidative stress, immunological assaults, biliary epithelial injuries, bile duct sclerosis, or anastomosis strictures post liver transplant.

Some embodiments of the present disclosure relate to the local delivery or administration to the lumen of damaged biliary ducts of an active agent by one or more means that provide immediate release and/or sustained release of the active agent, such that the active agent locally promotes increase in GSH production or inhibits GSH degradation. A sustained-release delivery means may be at least one of a biliary stent, a biliary implant, gel, or beads. For example, in some embodiments, the drug delivery means is a biodegradable biliary stent.

In some embodiments, a disclosed method utilizes a biodegradable biliary stent that provides sustained release of NAC and/or a derivative thereof, for example, L-NAC.

Further embodiments and the full scope of applicability of the present disclosure will become apparent from the detailed description given hereinafter.

BRIEF DESCRIPTION OF THE FIGURES

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings:

FIG. 1D are enlarged views of EHBDs of the 40 weeks old mice from FIGS. 1A and 1B. Scale bars: 50 μm;

FIGS. 2A-2B are H&E staining images of EHBDs obtained from Mdr2$^{-/-}$ mice at 2 weeks (2A) and 16 weeks (2B) of age that were either not treated or incubated in fresh cholangiocyte medium with or without 5 μM L-NAC for 24 hours. Scale bars: 10 μm. FIGS. 2C-2D are images of immunohistochemistry (IHC) stained and DAPI stained EHBDs sections taken from 2- and 16-week-old Mdr2$^{-/-}$ mice that were untreated or incubated in fresh cholangiocyte medium with or without the addition of 5 μM L-NAC. EHBDs were fixed and immune-stained for K19 and ZO-1. Scale bars: 5 μm.

DETAILED DESCRIPTION

Figure 1A:
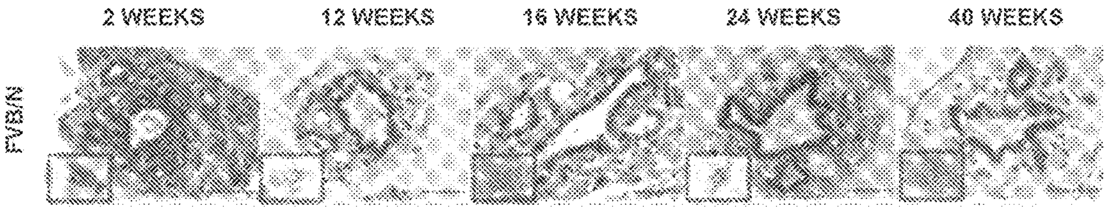
FIGS. 1A, 1B, 1D are exemplary histological staining images.

The biliary tree is composed of extrahepatic bile ducts (EHBDs) and intrahepatic bile ducts (IHBDs). The former, EHBDs, include the right and left hepatic ducts and their confluence. Extrahepatic and intrahepatic bile ducts are lined by highly specialized columnar epithelial cells, interchangeably termed herein "biliary epithelial cells (BECs)" or "cholangiocytes", and their wall is composed of dense collagenous tissue harboring scattered smooth muscular elements. The IHBDs include the bile ducts proximal to the right or left hepatic duct. The intrahepatic branching of the bile ducts is best visualized on a cholangiogram or biliary injection cast. There are peribiliary glands around the intrahepatic large bile ducts and extrahepatic bile ducts. The biliary tree is a conduit of bile secreted by hepatocytes, biliary epithelial cells and from the peribiliary glands.

The bile ducts and peribiliary glands play a number of physiological roles in the biliary system including contributing to about one-third of total bile secretion, participating in bile acid and water reabsorption, and mediating immune responses including innate immunity. The primary hepatic bile secreted by hepatocytes is modified by the BECs via a series of secretory and absorptive processes that provide additional bile water (BECs secrete ~40% of daily bile production in humans) The BECs interact with the immune system and microorganisms and are also involved in drug metabolism. To accomplish these functions, BECs display morphological and functional heterogeneity along the biliary tree.

A number of diseases affect the biliary tree (cholangiopathies), both the intrahepatic and extrahepatic bile ducts, though the pathological mechanisms involved, and the anatomical level of the biliary tree affected vary. For example, small interlobular bile ducts are mainly affected by a Th1-dominated microenvironment and cell-mediated immune response in primary biliary cholangitis (PBC), while a Th2-dominated microenvironment and increased numbers of regulatory T cells are the major features of IgG4-related sclerosing cholangitis which affects mainly the extrahepatic bile ducts.

While most studies are focused on the intrahepatic cholangiocytes injury, limited data in the literature directed to the damage of the extrahepatic biliary tree is disclosed, and cholangiopathies such as PSC remains poorly understood and without effective therapy. In her quest to uncover the mechanisms of injury and repair of the extrahepatic biliary tree in general, and in PSC disease state in particular, the present inventor envisaged a substantial role for glutathione (GSH) as injury mediator in EHBD injury. The present inventor hypothesized that a decreased GSH level is a significant mediator of initial cholangiocyte injury in Mdr2$^{-/-}$ mice model (a well-established model for PSC) that would lead to abnormal tight junctions and increased epithelial permeability, and that the resulting exposure of the injured epithelium to toxic bile acids would lead to injury propagation and fibrosis. By showing, in an Mdr2$^{-/-}$ mouse model, that local treatment with GSH, improved duct morphology even at advanced stages of injury, the present inventor confirmed and validated her hypothesis. In the Examples section herein, experimental results are disclosed showing that subjecting impaired EHBDs to means that are known to facilitate elevation of sub-normal GSH levels such as, but not limited to, N-acetyl-L-cysteine (L-NAC), a potential new therapy for extrahepatic biliary ducts damaged, e.g., in the course of a PSC disease, is provided.

Methods of Treatment

In one aspect, the present disclosure provides methods for treating damaged bile ducts in a subject, which damage may be cured, repaired, ameliorated and/or inhibited by at least one of elevating, restoring, or maintaining normal glutathione (GSH) levels in the biliary ducts, particularly in the biliary epithelial cells (BECs). Accordingly, at least some embodiments of a disclosed method, comprise steps and means for increasing GSH level, and/or inhibiting a decrease in GSH level in the BECs, thereby treating damaged bile ducts in the subject.

In some embodiments, the damaged bile ducts treated by a disclosed method are extrahepatic bile ducts (EHBDs).

In some embodiments, the damaged bile ducts treated by a disclosed method are intrahepatic bile ducts (IHBDs).

The tripeptide, γ-L-glutamyl-L-cysteinyl-glycine known as glutathione is the most important low molecular weight antioxidant synthesized in cells. Glutathione is capable of preventing damage to important cellular components caused by reactive oxygen species such as free radicals or peroxides, lipid peroxides, and heavy metals. It is synthesized by the addition of cysteine to glutamate followed by the addition of glycine. The sulfhydryl group, —SH, (also referred to as "thiol group") of the cysteine is involved in reduction and conjugation reactions that are usually considered as the most important functions of GSH. These reactions provide the means for removal of peroxides and many xenobiotic compounds. GSH is also involved in cell cycle regulation.

Glutathione exists in reduced state (GSH) and oxidized state as glutathione disulfide (GSSG), which is derived from two glutathione molecules. In the reduced state, the thiol group of the cysteinyl residue is a source of one reducing equivalent. The oxidized state is converted to the reduced state by NADPH in a reaction catalyzed by glutathione reductase. The ratio of reduced glutathione to oxidized glutathione within cells is a measure of cellular oxidative stress. In healthy cells and tissue (of any kind), more than 90% of the total glutathione pool in the cytosol is in the reduced form (GSH), with the remainder in the disulfide form. An increased GSSG-to-GSH ratio is indicative of oxidative stress. The normal GSH level is in the range of 1-10 mM. In most cells, the GSH concentration is about 1-2 mM.

Hepatocytes are a source of GSH that is exported to the plasma of other cells, thus, a normal level or concentration of hepatocyte GSH can be as high as about 10 mM. In cholangiocytes, basic concentrations of GSH, also referred to herein as "normal GSH level", is 5-10 times lower than GSH concentrations in hepatocytes, i.e., it is about 1-3 mM.

Damaged bile duct which presents, inter alia, sub-normal GSH levels in cholangiocytes may be treated, in accordance with a disclosed method, by way of elevating the decreased GSH levels so as to restore normal GSH levels (1-3 mM).

"Sub-normal GSH level", as referred to herein, is GSH concentration in cells such as cholangiocytes which is below 1 mM, for example, any concentration which is in the range of from about 0.2 mM to about 0.95 mM, e.g., 0.2 mM, 0.35 mM, 0.4 mM, 0.5 mM, 0.55 mM, 0.65 mM, 0.7 mM, 0.8 mM, 0.85 mM, or 0.9 mM.

In some embodiments, restoring normal GSH levels is provided by administration to a subject afflicted with damaged bile ducts of at least one active agent which promotes increased GSH production or synthesis in the cholangiocytes. Alternatively, or additionally, increasing of GSH levels may be obtained by way of adding external GSH. In some embodiments, increased GSH production and/or provision of external GSH is promoted or carried out locally, e.g., in the bile ducts themselves.

Distorted or non-normal duct morphology is sometimes observed in damaged bile ducts even in normal GSH levels. In some embodiments, deformed duct morphology may be cured by locally increasing GSH levels in cholangiocytes, even beyond normal levels, by means such as locally inducing increased GSH synthesis and/or locally administrating external GSH.

Bioavailability of orally consumed glutathione is poor due to the tripeptide being a substrate of proteases (peptidases) of the alimentary canal, and due to absence of specific carriers of glutathione at the level of cell membrane. Increasing GSH levels in cells may be obtained, for example, by increasing in the cytosol the bioavailability of one or more of its building blocks such as, but not limited to, cysteine. Cysteine amounts can be increased by provision of, for example, the nontoxic precursor N-acetyl L-cysteine (L-NAC), a salt thereof (e.g., an alkali metal salt), or any derivative thereof that can be converted to cysteine and/or can be incorporated into the three-peptide so as to provide an active GSH derivative. L-NAC is known for its anti-oxidative effects and ability to protect cells from oxidative stress. Non-limiting examples of L-NAC derivatives include N-acetyl-L-cysteine amide and S-nitrosothiol-containing NAC molecules such as S-nitroso-N-acetyl cysteine (NAC-SNO) and S-nitroso-captopril (captopril-SNO).

In some embodiments, the active agent used for increasing GSH levels, in accordance with a disclose method, is L-NAC.

Additional active agents that may be employed for elevating GSH levels in cells include compounds such as sulforaphane (an Nrf2 activator that increases GSH), alpha lipoic acid, calcitriol (1,2,5-dihydroxy vitamin $D_3$; the active metabolite of vitamin $D_3$, which increases glutathione levels in the brain and appears to be a catalyst for glutathione production), and S-adenosylmethionine (SAMe; increases cellular glutathione content in persons suffering from a disease-related glutathione deficiency).

In accordance with the present disclosure, biliary ducts damage associated with reduced GSH levels may be prevented or inhibited in a subject, for example, a subject diagnosed as afflicted with a biliary or liver disease or disorder, e.g., when diagnosed at very early stages of the disease or the disorder, and/or a subject undergoing liver transplantation. Prevention or inhibition of expected damage to biliary ducts may be obtained, in accordance with a disclosed method, by way of at least one of elevating, restoring, or maintaining normal GSH levels in the biliary ducts, particularly in BECs.

In some embodiments, elevating GSH levels, restoring normal GSH levels and/or maintaining normal GSH levels is provided by a local biliary intervention, for example, by locally administrating to the damaged bile ducts of at least one active agent which either promotes increase in GSH production or inhibits GSH degradation.

In some embodiments, the biliary ducts being locally treated as preventive measures or in the course of a cholangiopathy stage are the EHBDs.

The human EHBDs can be reached with endoscopic retrograde pancreatography (ERCP), basically, an upper endoscopy procedure that can reach the papilla (the connection of the bile ducts to the small bowel) and cannulate it as is routinely done to either insert a mechanical stent at a narrowed or obstructed area (e.g., as a temporary measure before liver transplant), to inject a contrast agent to image the biliary tree, or to remove a blocking stone. Endoscopic retrograde pancreatography, which is not a surgery procedure, is one non-limiting example of an optional delivery means for local administration to the biliary tree of an active agent that supports increasing, restoring and/or maintaining normal (or basic) GSH levels, in accordance with some embodiments of the present disclosure.

Local administration of active agents to the biliary tree may also be facilitated by percutaneous transhepatic cholangiography (PTC). Percutaneous transhepatic cholangiography is a procedure performed for diagnostic and/or therapeutic purposes by, first, accessing the biliary tree with a needle, followed shortly afterward by a catheter for percutaneous biliary drainage (PBD). At some point during the procedure, contrast may be injected into one or more bile ducts (to obtain a cholangiogram) and also possibly into the duodenum for the purpose of visualizing the anatomy of the biliary tract, e.g., by X-ray. The procedure may be performed with fluoroscopic guidance only or also with ultrasound (US) guidance. PTC is performed mostly for therapeutic purposes in the setting of suspected or already confirmed bile duct obstruction and/or to obtain diagnostic specimens, particularly when ERCP is not an option or has been unsuccessful.

Both ERCP and PTC may be the clinical procedure to introduce biliary stents into EHBDs.

A biliary stent (also known as a "bile duct stent") is a flexible tube specially designed to hold the bile duct open. Benign strictures are traditionally managed with balloon dilatation and insertion of stents so as to reduce or eliminate blocked ducts. Once a stent is in place in the obstructed area, the stent is designed to expand and open the channel so that fluids can continue flowing to the intestine. The biliary stenting is performed either with plastic or metal stents, and their replacement is recommended after 3-6 months. Metal and plastic stents have been associated, however, with various complications including difficult extraction, migration and hyperplasia. Patients with long stayed, forgotten biliary stents are inevitably treated by surgical intervention.

Biodegradable stents made of biocompatible and biodegradable materials remedy at least some of the problems associated with metal and plastic stents. Biodegradable stents have reduced the requirement for reintervention and can be placed in cases of altered surgical anatomy.

A biomaterial is designed to be implanted or incorporated into a living biological system. A biomaterial is exchangeable also referred to herein as "bioabsorbable matrix". Biomaterials can be inert, bioactive, and/or biodegradable. Inert materials do not trigger any reaction in the host, bioactive materials can ensure stable and lasting performance, and biodegradable materials can decompose as the product of natural factors such as bacteria or can be chemically degraded. Synthetic polymers and magnesium-based materials (e.g., magnesium alloys) are commonly used in biodegradable applications. The synthetic polymers include, but are not limited to, polylactic acid, polyglycolic acid, polycaprolactone, polydioxanone and poly (lactic-co-glycolic acid). Polymeric biomaterials have several advantages: they are elastic, have low densities and relatively easy to manufacture. The polymers used in biomaterials degrade in a hydrolytic process into low molecular weight molecules that can be metabolized by the body. Biodegradable materials useful for biodegradable stents have at least the following qualities: (i) ability to maintain sufficient expansive force until the stenosis is resolved; (ii) not toxic; (iii) not inducing an inflammatory response in the surrounding tissue; (iv) easily metabolizable in the body after they fulfill their function; (v) easily processed and never leaving traces; and (vi) easy to sterilize.

Exemplary biodegradable stents are constructed with woven poly-dioxanone, a biodegradable synthetic polymer that has been more traditionally used in absorbable surgical sutures.

Delivering a drug in a very localized and controlled mannered may be obtained by means (devices) that incorporate a drug into a bioabsorbable matrix in which the release and subsequent availability of the drug is determined by the speed at which the polymer containing the drug degrades. Drug-eluting stents (DES) such as those used for some coronary applications, are non-limiting examples of biodegradable means for local delivery of drugs that may find use in biliary applications.

Some embodiments of the present disclosure pertain to the use of a biodegradable stent for local administration of an active agent that increases, restores and/or maintains normal GSH levels. In some embodiments, the biodegradable stent provides immediate release of at least one active agent. In some embodiments, the biodegradable stent provides sustained release of at least one active agent, e.g., over several hours, days, weeks or months.

In some embodiments, the active agent which is locally delivered to EHBDs so as to promote increase in GSH level in cholangiocytes is L-NAC and/or a derivative thereof loaded onto or impregnated into a biliary stent.

In exemplary embodiments, sustained release of, e.g., L-NAC, over several months is provided by a biodegradable biliary stent, which may be allowed to decompose in the ducts or may be removed or replaced with a new one if the active agent is still required.

In an aspect of the present disclosure, there is provided a method for local treatment of damaged biliary duct resulting from a biliary disease and/or a basic injury of biliary epithelial cells (BECs) and/or bile duct lumen, which damage may be cured, ameliorated, prevented or inhibited by locally administrating and, thereby, directly contacting the biliary ducts lumen with a pharmaceutically effective amount of one or more one active agents which promote increase in GSH production or inhibit GSH degradation.

In some exemplary embodiments, L-NAC and/or a derivative thereof is locally delivered to the damaged bile duct using any of the means described herein, to thereby promote increase in GSH production.

Bile duct damage which may be treated by a disclosed method may directly or indirectly be caused by various cholangiopathies and/or by cholestasis.

Cholestasis is defined as a condition caused by rapidly developing (acute) or long-term (chronic) interruption in the excretion of bile. The term is taken from the Greek chole, bile, and stasis, standing still. Cholestasis is caused by obstruction within the liver (intrahepatic) or outside the liver (extrahepatic). The obstruction causes bile salts, the bile pigment bilirubin, and fats (lipids) to accumulate in the blood stream instead of being eliminated normally.

Intrahepatic cholestasis is characterized by widespread blockage of small ducts or by diseases or disorders, such as hepatitis, that impair the body's ability to eliminate bile. Intrahepatic cholestasis may also be associated with medications that can produce symptoms resembling hepatitis (for example, Phenothiazine-derivative drugs, including chlorpromazine) Intrahepatic cholestasis may be caused by alcoholic liver disease, primary biliary cirrhosis, cancer that has spread (metastasized) from another part of the body, and a number of rare disorders.

Extrahepatic cholestasis can occur as a side effect of many medications, e.g., a complication of chemotherapy or consumption of chlorpromazine (Thorazine), a tranquilizer and antinausea drug. It can also occur as a complication of surgery, for example, cholestasis may result, e.g., by strictures in the bile after liver transplant, serious injury, tissue-destroying infection, or intravenous feeding. Extrahepatic cholestasis can be caused by conditions such as tumors and gallstones that block the flow of bile from the gallbladder to the first part of the small intestine(duodenum).

The two major types of drug-induced cholestasis are direct toxic injury and reactions unique to an individual (idiosyncratic reactions). In direct toxic injury, the severity of symptoms parallels the amount of medication involved. This condition may develop a short time after treatment begins, it follows a predictable pattern, and usually causes liver damage.

Symptoms of both intrahepatic and extrahepatic cholestasis include a yellow jaundice (a yellow coloring of the skin and eyes due to a very high level of bilirubin (bile pigment) in the bloodstream), dark urine, and pale stools. Some patients who have cholestasis experience symptoms only after infection develops, but chronic bile-duct obstruction always leads to cirrhosis. It may also cause osteoporosis (fragile bones) or osteomalacia (soft bones).

Both intrahepatic and extrahepatic cholestasis may the outcome of a cholangiopathy, and/or a non-cholagiopathic disorder or conditions such as pathogens (viruses, bacteria, parasites), stress, oxidative stress, and immunological assaults, as well as biliary epithelial injuries from necrosis, apoptosis, and hyperplasia.

The serum concentrations of conjugated bilirubin, bile salts (components of bile) and the enzymes alkaline phosphatase and gamma-glutamyl-transferase (GGT), both of which originate from damaged BECs, are the most commonly measured markers for cholestasis, with alkaline phosphatase and GGT being the sole markers for early stages of cholestasis without full obstruction of bile flow.

The term "cholangiopathy", as used herein, refers to any disease of the bile ducts. Cholangiopathies may be divided into several categories according to the pathogenetic mechanism involved. However, in many cholangiopathies, more than one pathogenetic mechanism is operative. A cholangiopathy is most commonly classified as being one or more of (i) immune-mediated cholangiopathy; (ii) infectious cholangiopathy; (iii) genetic cholangiopathy; (iv) ischemic cholangiopathy; and (v) drug- or toxin-induced cholangiopathy.

In immune-mediated cholangiopathies, the biliary tree is affected by immunological assaults, and lymphoplasmacytic infiltration is evident around the damaged bile ducts. Primary biliary cirrhosis (PBC) and primary sclerosing cholangitis (PSC) are representative immune-mediated cholangiopathies. Autoimmune pathogenesis is operative in PBC and PSC. Biliary innate immunity is also involved in the pathogenesis of PBC and biliary atresia (BA). Intrahepatic small bile ducts and bile ductules are a main target in graft-versus-host disease and also hepatic allograft rejection. IgG4-related sclerosing cholangitis is also associated with altered immunity. The anatomical level of the biliary tree affected is different among these immune-mediated cholangiopathies.

In infectious cholangiopathies, the biliary tree is affected by several types of infectious diseases, such as bacterial, fungal, protozoan, parasitic, and viral cholangitis. Stagnation of bile due to biliary stenosis or obliteration may be followed by bacterial cholangitis, frequently with sepsis or abscess formation. Cholangiocarcinoma is a serious complication of parasitic cholangitis. Hepatolithiasis is predominantly a disease of the Far East and is causally related to infectious cholangitis, especially bacterial cholangitis.

In genetic cholangiopathies, genetic alterations affecting the biliary tree manifest, inter alia, as biliary dilatation, bile duct paucity, obstruction, proliferation and stone formation. Caroli's disease with congenital hepatic fibrosis (CHF) is a representative genetic cholangiopathy. Some cases of biliary atresia (BA) also belong to this category.

Ischemic cholangiopathy is defined as focal or extensive damage to bile ducts due to an impaired blood supply. Most causes of bile duct ischemia are iatrogenic, though some systemic vascular diseases also cause this type of cholangiopathy. Ischemic bile duct injury may occur when small hepatic arteries or the peribiliary vascular plexus are injured or when all possible sources of arterial blood supply are interrupted. Ischemic biliary injury may take the form of bile duct necrosis, bile leakage, biloma, bile duct fibrosis, or stenosis. Ischemic cholangiopathy is a serious complication during liver transplantation and can occur at the site of anastomosis in which case it is usually treated with local stent in an attempt to dilate the stricture, which does not have an effective therapy.

In drug- or toxin-induced cholangiopathies, bile ducts, particularly interlobular bile ducts, are occasionally affected by drug-induced hepatobiliary damage. Drug-induced cholangiopathy herein includes, for example, drug-induced vanishing bile duct syndrome (VBDS), drug-induced bile duct injury, drug-induced ductopenia and disappearing intrahepatic bile ducts.

Drug-induced bile duct injury refers to a subcategory of idiosyncratic cholestatic or mixed type (hepatic and cholestatic) injury, characterized by severe damage to the biliary epithelium and often accompanied by the disruption of the biliary tree architecture. Drug-induced bile duct injury in most cases affects the biliary epithelium of interlobular ducts (e.g., injury caused by amoxicillin/clavulanic acid, carbamazepine), thereby sharing common pathophysiological features with other cholangiopathies. Some drugs (e.g., fluorodeoxyuridines, 5-fluorouracil) selectively damage larger ducts (e.g. the common hepatic duct). Drug-induced injury is dose-dependent and thought to be the result of the intrinsic toxicity of certain drugs with a minor immune component. Some cases of drug-induced bile duct injury presenting with progressive ductopenia and cholangitis and prolonged cholestasis mimic PBC and also PSC.

In toxin-induced cholangiopathy, cytotoxic or cytopathic bile duct injury may be produced by toxic substances such as α-naphthylisothiocyanate, 4,4'-diaminodiphenylmethane, and paraquat.

In some biliary diseases such as PBC and chronic ductopenic allograft rejection, the ongoing apoptosis of BECs is important for progressive bile duct loss.

The term "cholangitis" is used herein for inflammatory damage to bile ducts. Cholangitis is characterized by biliary epithelial damage with inflammatory cell infiltration. An inflammatory response directed predominantly at cholangiocytes is usually associated with prolonged cholestasis that can progress to bile duct degeneration and loss. Some cholangitis is also associated with ductal and periductal fibrosis. Exemplary forms of cholangitis include suppurative cholangitis (histologically identified by the presence of numerous polymorphonuclear cells around and within the wall as well as within the lumen of the ducts; occasionally associated with abscess formation (cholangitic abscess)), and nonsuppurative cholangitis which includes a spectrum of bile duct inflammation such as granulomatous cholangitis, lymphoid cholangitis, fibrous cholangitis, and pleomorphic cholangitis, according to the predominant type of inflammatory reaction present.

In some embodiments, a contemplated method is applied for treating damages in the biliary ducts of a subject afflicted with PSC. Primary sclerosing cholangitis is a rare and chronic liver disease characterized by a progressive course of inflammation and fibrosis of the intrahepatic and extrahepatic bile ducts, primarily affecting large ducts and having a proclivity toward males, with a median age of presentation of ~40 years. The underlying cause of the inflammation is believed to be an autoimmune response. Progressive fibrostenotic stricturing of the biliary tree causes important clinical sequelae, including liver cirrhosis, portal hypertension, and end-stage liver disease (ESLD).

To date, no approved or proven therapy exists for PSC, with pharmacotherapy aimed at treating symptoms and managing complications Immunosuppressants, bile salts, chelators (e.g., cholestyramine for pruritus), and steroids have not shown significant benefit in clinical trials, and treatment of PSC is still an unmet need, particularly as at least a third of patients will experience liver-related death without hepatic transplantation.

Primary sclerosing cholangitis can affect solely the intrahepatic bile ducts or both the intra- and extra-hepatic bile ducts. Thus far, the vast majority of research in the field has been focused on the intrahepatic disease. An IHBD and an EHBD arise from different primordia (initial phases): the cranial portion of the endodermal diverticulum gives rise to the liver and the IHBD while the caudal portion develops into the EHBD, and it has been shown that the cranial and caudal portions comprise different types of cells. Thus, the injury processes are likely to differ between the two. Moreover, the intrahepatic cholangiocytes are in a different environment, surrounded by hepatocytes which have higher GSH levels, compared to the extrahepatic cholangiocytes which are surrounded by extracellular matrix and fibroblasts. This is most likely relevant to the repair mechanisms. The present disclosure provides, for the first time, a repair or cure means for extrahepatic cholangiocytes injured in a subject inflicted with PSC.

In some embodiments, a contemplated method is applied for treating damages in the biliary ducts of a subject afflicted with primary biliary cholangitis (PBC).

Primary biliary cholangitis (often referred to as primary biliary cirrhosis) is a chronic, or long lasting, progressive liver disorder that mostly affects women and usually appears during middle age. PBC leads to inflammation and scarring of the small bile ducts. When PBC is very severe, it can lead to yellow discoloration of the skin (jaundice). If PBC is untreated, it can lead to cirrhosis, or scarring of the entire liver, which can lead to liver failure. PBC is divided into four stages, with stage 1 being early disease, where this is no significant scarring, to stage 4, which is defined by cirrhosis. Although the exact cause of PBC is unknown, it is most likely due to a combination of factors such as autoimmune, genetic, and environmental factors. The most common symptoms of PBC are fatigue, pruritus (itchiness) and jaundice. Jaundice usually happens when the liver is so damaged that the normal function of the liver is impaired. Complications of PBC include portal hypertension (ascites, varices, hepatic encephalopathy), fat malabsorption, fat deposits, and osteoporosis/osteomalacia. To date, no approved or proven effective therapy exists for damaged biliary ducts in patients inflicted with PBC, and in absence of treatment, PBC may eventually lead to liver failure and require liver transplantation.

In some embodiments, a contemplated method is applied for treating damages in the biliary ducts of a subject afflicted with bile duct anastomosis strictures post liver transplant. Anastomosis, in the context of these embodiments, refers to a surgical connection between tubular structures such as blood vessels, bile ducts or loops of intestine.

Stricture of a bile duct is an abnormal narrowing of the duct due. Herein, "stricture" encompasses both the process of narrowing and the narrowed part itself. Biliary strictures are a well-known and a common complication of both living donor liver transplant (LDLT) and deceased donor liver transplant (DDLT) and account for more than 50% of all biliary complications of liver transplant. The factors that most commonly contribute to stricture formation include the surgical reconstruction technique (e.g., duct-to-duct anastomosis), type of liver transplant procedure (LDLTs are more prone to strictures than DDLTs), and development of hepatic arterial thrombosis. Biliary strictures are classified as anastomotic strictures or non-anastomotic strictures, depending on their location. Anastomotic strictures are segmental, single, short and/or focal narrowing around a biliary anastomosis and are thought to result primarily from fibrotic healing. Currently, the incidence of anastomotic strictures is reported to be approximately 13%.

Biliary strictures can occur months to years after liver transplant, but they most commonly present within the first year, with a mean interval from transplant to time of presentation of 5 to 8 months. Strictures that occur early after liver transplant usually result from technical problems in the surgery itself, whereas strictures that develop later arise mainly from vascular insufficiency, immunologic causes, or problems with healing and fibrosis.

Biliary strictures account for significant morbidity and mortality after liver transplant. Of note, current treatment in the art is most commonly endoscopic therapy comprising repeated dilatation of the strictures until they open. Some cases require surgical correction, and in some cases repeated liver transplantation is required.

In some embodiments, a contemplated method is applied for treating damages in the biliary ducts of a subject afflicted with IgG4-related sclerosing cholangitis.

Immunoglobulin G4-related disease (IgG4-RD) is an immune multi-system-mediated disorder of unknown etiology, and has a broad spectrum of clinical manifestations, depending on the organ or system involved. This disorder is characterized by fibro-inflammatory activity that may present as mass-forming lesions. The condition can affect one or multiple organs at the same time and is associated with elevated serum IgG4 in most cases. IgG4 sclerosing cholangitis (IgG4-SC) is the biliary manifestation of IgG4-RD. Patients with IgG4-SC display dense infiltration of IgG4-positive plasma cells with extensive fibrosis in the bile duct wall. Circular and symmetrical thickening of the bile duct wall is observed in areas without stenosis that appear normal on cholangiography, as well as in the stenotic areas. Awareness of IgG4-SC is important as it may mimic other benign and malignant conditions, including PSC and cholangiocarcinoma (CCA). IgG4-SC has a preponderance for older males and may exhibit a variety of presentations including abdominal pain, jaundice, pruritus and weight loss.

In some embodiments, a contemplated method is applied for treating damages in the biliary ducts of a subject afflicted with biliary atresia.

Biliary atresia (BA) is a rare disease of the liver and bile ducts that occurs in infants. Symptoms of the disease appear or develop about two to eight weeks after birth. When a baby has BA, bile flow from the liver to the gallbladder is blocked. This causes the bile to be trapped inside the liver, quickly causing damage and scarring of the liver cells (cirrhosis), and eventually liver failure. The causes of biliary atresia are not completely understood. For some children, biliary atresia may occur because the bile ducts did not form properly during pregnancy. For other children with biliary atresia, the bile ducts may be damaged by the body's immune system in response to a viral infection acquired after birth.

Symptoms of BA include jaundice usually developing two or three weeks after birth, dark urine, acholic stools (clay-colored stools), swollen abdomen, a firm, enlarged liver, weight loss and irritability, which develop when the level of jaundice increases.

Biliary atresia cannot be treated with medication. A Kasai procedure or hepatoportoenterostomy is done. The Kasai procedure is an operation to re-establish bile flow from the liver into the intestine, in which the damaged extrahepatic ducts are removed and smaller ducts that are still open and draining bile are attached to a loop of intestine so that bile can flow directly from the remaining healthy bile ducts into the intestine.

Although the Kasai procedure is successful in 60% to 85% of the patients, allowing babies to grow and have fairly good health for several, sometimes for many, years, it is not a cure for biliary atresia. In 15-40% of patients the Kasai procedure does not work, and liver transplantation may be needed.

Treating a damaged bile ducts, as referred to in the context of embodiments described herein, encompasses ameliorating, inhibiting the progression of, delaying worsening of, and even completely preventing the development of any one of more of the damages in biliary ducts as defined herein, particularly, but not exclusively, by addressing abnormal GSH levels in cholangiocytes. In a broad sense, "treatment" refers to a therapeutic intervention that ameliorates a sign or symptom of a disease or a pathological condition caused by or associated with biliary duct damage.

"Administration", as referred to herein, is provision or introduction into a subject by a chosen route of one or more active agents for therapeutic or diagnostic purposes. For example, administration is providing to a subject to at least one active agent which promote at least one of elevated glutathione (GSH) levels, restoration of normal GSH levels, or maintenance of normal GSH levels in the biliary ducts. Some embodiments of the present disclosure pertain to local administration of an active agent, for example, L-NAC directly to damaged biliary ducts.

Kits

In still a further aspect, the present disclosure relates to a kit comprising at least one active agent (a drug) and a drug-release means that releases the drug directly in the biliary tree, and, optionally, instructions and means for administration of the drug releasing means to a subject in need thereof.

In some embodiments, a contemplated kit comprises a biodegradable biliary stent as the drug releasing means. In exemplary embodiments, the biodegradable biliary stent comprises L-NAC.

A contemplated kit is useful in the treatment of damaged bile ducts and/or in prevention or inhibition of damage to bile ducts.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the present disclosure.

As used herein the term "about" refers to ±10%.

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments described may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Various embodiments and aspects of the present disclosure as delineated hereinabove and as claimed in the claims section below find experimental support in the following examples.

EXAMPLES

Reference is now made to the following examples, which together with the above description illustrate some embodiments of the disclosure in a non-limiting fashion.

Generally, the nomenclature used herein, and the laboratory procedures utilized in the present disclosure include molecular, chemical, biochemical, and/or microbiological, and clinical procedures. Such techniques are thoroughly explained in the literature. See for example, Guide to Research Techniques in Neuroscience (Second Edition), Matt 2015; Elsevier's Integrated Review Biochemistry (Second Edition), 2012. Other general references are provided throughout this document. The procedures therein are believed to be well known in the art and are provided for the convenience of the reader.

Materials and Methods

(i) Mdr2 Knockout Mice

The homozygote, multidrug resistance protein 2 knockout mouse (Mdr2KO or $Mdr2^{-/-}$, also known as $Abcb4^{-/-}$) lacks the protein MDR2, a canalicular phospholipid flippase that causes a complete absence of phosphatidylcholine in bile. $Mdr2^{-/-}$ mice are a well-established model for biliary ducts diseases resulting from, or associated with, highly toxic bile. Multidrug resistance P-glycoproteins, Mdr2 in mouse and MDR3 in human, are choline-containing phospholipid phosphatidylcholine (PC) transporters. In the liver, Mdr2/MDR3 are involved in the translocation of PC from the inner leaflet to the outer leaflet of the canalicular membrane of hepatocytes for direct extraction by bile acids. Bile acids and PC are essential components in the bile that form bile acid containing micelles to thereby reduce the toxic detergent activity of bile acid for hepatocytes and cholangiocytes and to establish physiological bile flow. Mdr2 knockout mouse successively develops liver inflammation, hepatic fibrosis, and hepatocellular carcinoma (HCC) at late ages. The pathogenesis in $Mdr2^{-/-}$ mice is commonly considered to be caused by increased levels of free toxic bile acids in the biliary canaliculus, which damages hepatocytes and cholangiocytes and provokes liver inflammation. This cholangiopathy is similar to human PSC.

The wild type and Mdr2 knockout mice used in embodiments described herein are male and female mice of FVB genetic background (FVB/N and FVB/$Mdr2^{-/-}$ mice, respectively). All mice were maintained under specific pathogen-free conditions with a 12-hour-light-dark cycle and permitted ad libitum consumption of water and a standard chow. FVB/$Mdr2^{-/-}$ mice are reproducible model of spontaneously progressive chronic biliary liver disease associated with fibrosis, with histological lesions closely resembling human PSC. Though the $Mdr2^{-/-}$ mouse is well-established for the investigation of PSC, little is known about EHBD injury in this model.

(ii) Bile Duct Explant Culture

Intact extrahepatic bile ducts (EHBDs) from 2-week (N≥12) and 16-week (N≥5) old mice were dissected, placed in ice-cold V-7 cold preservation buffer (Vitron) followed by incubation in cholangiocyte medium (also termed herein "BEC medium"), according to a modification of the protocol described by Karjoo and Wells (Isolation of neonatal extrahepatic cholangiocytes. *J. Vis. Exp.* 2014). Ducts were placed on roller inserts, treated with N-Acetyl-L-cysteine (L-NAC) and other compounds as noted below, and cultured in a high oxygenation Vitron Dynamic Organ Culture Incubator at 37° C., in 95% $O_2$ and 5% $CO_2$, for 1-3 days. In the incubator (designed to optimally incubate tissue slices), the explants rotated and were exposed to alternating periods in medium and 95% oxygen/5% $CO_2$. Thin slices of tissue remained viable without visible damage or evidence of necrosis or apoptosis for at least 3 days.

(iii) Human Samples

Human samples for assessing the effect of local L-NAC treatment are obtained from surgeries in which the extrahepatic biliary tree is removed, for example, via Kasai portoenterostomy, or obtained from PSC patients and patients with other cholangiopathies (e.g., PBC, biliary atresia), and pediatric patients transplanted for metabolic diseases and having normal EHBDs, which are dissected in part due to Roux-en-Y anastomosis. Human explants are kept in the high oxygenation Vitron Dynamic Organ Culture incubator.

For each duct, a small piece is dissected and fixed for internal pre-treatment comparison.

(iv) Histological Staining, Immunostaining and DAPI Staining of Dissected Biliary Ducts 1. Histological H&E staining of cells of ducts tissue was performed according to standard staining protocol, using two dyes: the basic dye haemotoxylin and the acidic dye eosin. Eosin reacted with cationic or basic components (also termed "acidophilic") and stained red or pink acidophilic structures (e.g., cytoplasmic proteins, intracellular membranes, and extracellular fibers). Haematoxylin, reacted with anionic or acidic components (also termed "basophilic") in cells and, when used in combination with aluminum ions ($Al^{3+}$), stained purplish blue basophilic structures (e.g., the nucleic acids in the nucleus and parts of the cytoplasm that contain RNA (e.g., ribosomes and the rough endoplasmic reticulum)). EHBDs were fixed in 4% paraformaldehyde (PFA) and embedded in paraffin, then sections (4-μm thick) were cut and stained with H&E.

2. Histologic staining of fixed mice liver slices was conducted with a Sirius Red Stain Kit in order to visualize connective tissues, collagen and fibers, and observe fibrosis due to e.g., inflammation. In bright field microscopy (standard light microscopy) the following can be observed: the nuclei stain in yellow; the cytoplasm stains yellow; collagen fibers stain red; muscular fibers stain yellow; and red blood cells in yellow.

3. Immunostaining or immunohistochemistry (IHC), which combines anatomical, immunological and biochemical techniques, was conducted in order to image discrete components in EHBDs tissues by using appropriately labeled antibodies that bind specifically to their target antigens in situ Immunohistochemistry made it possible to visualize the high-resolution distribution and localization of specific cellular components within cholangiocytes and within their proper histological context Immunostaining methodology included two main steps: sample preparation and sample staining. In the preparation step, ducts were fixed at 4% PFA for the preservation of cell morphology and tissue architecture. Thin sections of tissues (4-μm thick) attached to individual glass slides where then immunostained as described e.g., in Dipaola et al., 2013 (*Hepatology* 58:1486-1496, 2013), using antibodies against the cholangiocyte marker keratin 19 (K19, 1:10, Developmental Studies Hybridoma Bank, TROMAIII) and ZO-1 tight junction protein (anti-ZO1 antibody ab96587; Abcam).

4. Staining with 4', 6-diamidino-2-phenylindole (DAPI; D1306, Invitrogen), a fluorescent dye which binds preferentially to the AT-rich regions of dsDNA, was conducted to 4% PFA fixed slices of EHBDs tissues in order to visualize nuclear DNA in the fixed cells, and for assessing gross cell morphology.

Images of histologically stained, DAPI stained and/or immunostained duct and liver tissues were taken with Zeiss Axio Imager Z2 ApoTome microscope using the ZEN blue edition software at ×20 and ×40 magnifications, or Leica SP5 inverted confocal microscope at 340 magnification using LAS-AF software, at ×63 oil objective. Images were analyzed using ImageJ software.

(v) Glutathione (GSH) Measurement

Glutathione in tissue (from mouse liver and bile ducts) is measured using a Sigma-Aldrich kit. Tissue extracts are washed with PBS and homogenized in PBS with ethylene diamine tetraacetic acid (2 mM). The assay is performed per the manufacturer's protocol.

Example 1

MDR2 Knockout (Mdr2$^{-/-}$) Mice Can Model Injured Extrahepatic Bile Duct in Human Primary Sclerosing Cholangitis (PSC)

The Mdr2$^{-/-}$ (MDR2 knockout) mouse is a well-established model for PSC. However, there is very limited data in the literature related to extrahepatic bile ducts (EHBDs) injury, in this mice model specifically, and in PSC in general, as most studies thus far were focused on intrahepatic cholangiocytes injury. Assessing the EHBDs damage in Mdr2$^{-/-}$ mice is of high importance as intra- and extrahepatic cholangiocytes have different embryonic origins, and there are likely different repair mechanisms of the intra- vs. extrahepatic cholangiocytes due, e.g., to the difference in cell types and tissues that surround these two types of ducts, as well as different GSH baseline levels of the liver vs. EHBDs (the total GSH level in the liver is at least 5 times higher than in the extrahepatic bile ducts).

Figure 1B:
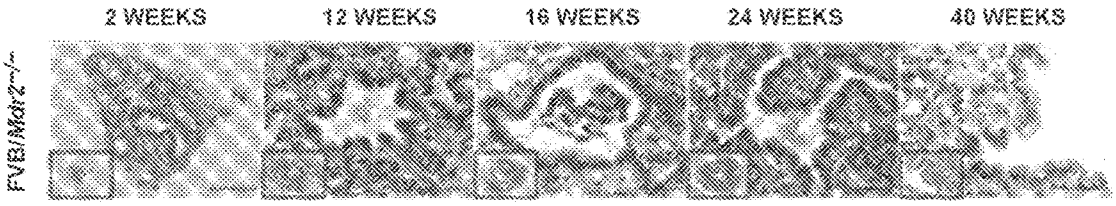
Figure 1C:
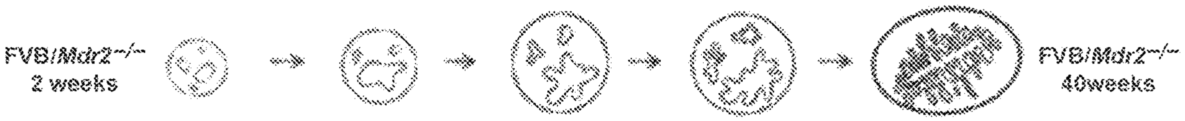
FIG. 1C is a sketch of extrahepatic bile ducts (EHBDs). EHBDs were dissected from 2-, 12-, 16-, 24-, and 40-week old wild type mice (FVB/N) (1A), and Mdr2 knockout mice (FVB/Mdr2$^{-/-}$) (1B) of the corresponding age, sectioned and stained with hematoxylin and eosin (H&E staining). Small boxes in FIGS. 1A and 1B show lower magnifications of the duct to demonstrate whole duct morphology. Scale bars: 50 μm. The sketches in FIG. 1C are of a FVB/Mdr2$^{-/-}$ mouse schematically demonstrating progressive lumen irregularities.
Figure 1D:
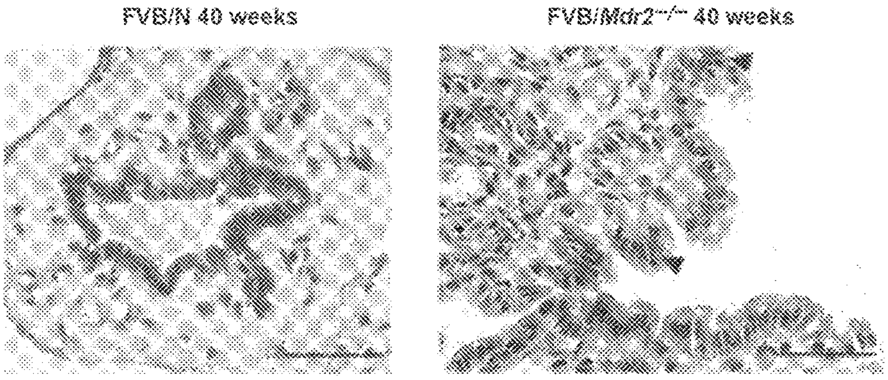

Extrahepatic biliary ducts damage in Mdr2$^{-/-}$ mice was confirmed via histological analysis. The EHBDs of Mdr2$^{-/-}$ (FVB/Mdr2$^{-/-}$) mice and wild type (FVB/N) mice aged 2 to 40 weeks were dissected and histologically stained (H&E staining). N≥3 for each age. Exemplary images of H&E stained EHBDs of 2-, 12-, 16-, 24-, and 40-week old wild type (WT) and MDR2 knockout mice are presented in FIGS. 1A-1D. Sections of EHBDs from WT mice showed stable and normal duct morphology from age 2 to 40 weeks, with oval duct lumens set in bland fibrous stroma, lined by regular, cuboidal to columnar biliary epithelial cells (FIG. 1A). In contrast, Mdr2$^{-/-}$ EHBDs demonstrated progressive luminal irregularities and reactive epithelial changes, including nuclear crowding with coarse chromatin changes, focal pseudo-stratification, and epithelial sloughing, together with mild periductal inflammation (FIG. 1B, and high magnification of 40-week old mice shown in FIG. 1D). The sketches of Mdr2$^{-/-}$ EHBD shown in FIG. 1C, demonstrate progressive lumen irregularities. The injury was already visible at 2 weeks and progressed over time. By 40 weeks, the EHBDs of the Mdr2$^{-/-}$ mice were severely damaged, resembling the pathology of human end-stage PSC.

It is shown herein that $Mdr2^{-/-}$ mice develop substantial EHBD injury over time, already starting at age two weeks. The injury resembles human PSC, and is characterized by progressive hyperplasia, luminal complexity, epithelial injury, reactive changes and periductal inflammation. This is the first report that describes EHBD histology in this mouse model. The features of the injury suggest that $Mdr2^{-/-}$ mice can be used as a PSC model also in terms of extrahepatic bile duct disease for medical research and drug testing.

Example 2

Ex-Vivo Repairing of Early-Stage Injured Extrahepatic Bile Duct by L-NAC

N-acetyl-L-cysteine (L-NAC), a precursor of glutathione, has choleretic properties (namely, it increase the volume of secretion of bile from the liver as well as the amount of solids secreted) based on its osmotic gradient in bile duct lumen. L-NAC also decreases the viscosity of canine bile, and its hepatoprotective effects have been documented in CC14 induced liver damage, in a chronic bile duct ligation model, and in biliatresone-induced bile duct injury in livestock.

Decrease in normal GSH level in biliary ducts may lead to destabilization of microtubules, loss of cell polarity, abnormal tight junctions, increased permeability and lumen obstruction. Loss of tight junctions may result in leakage of bile into the submucosa, leading to formation of fibrosis in the submucosa. Lumen patency can be evaluated by cholangiocyte marker keratin 19 (K19) staining and staining for tight junction proteins such as the Zonula occludens-1 (ZO-1), also known as Tight junction protein-1, claudin and E-cadherin.

In order to determine whether L-NAC treatment can mediate repair of EHBD damage in $Mdr2^{-/-}$ mice, assumingly by means of increasing GSH, EHBD explants from 2- and 16-week old $Mdr2^{-/-}$ mice were cultured in a rotating high-oxygenation Vitron Dynamic Organ Culture Incubator at 37° C., in 95% $O_2$ and 5% $CO_2$ incubator with fresh cholangiocyte medium (BEC) with or without the addition of 5 μM L-NAC for 24 hours (see Material and Methods above). Untreated ducts (which have been provided with fresh BEC) and ducts cultured only in fresh 5% BEC media served as controls. $N \geq 5$ for each group. Fixed sections of EHBDs were histologically sained with H&E staining, immune-stained, and DAPI stained as described in Materials and Methods. The results are presented in FIGS. 2A-2D.

Figure 2A:
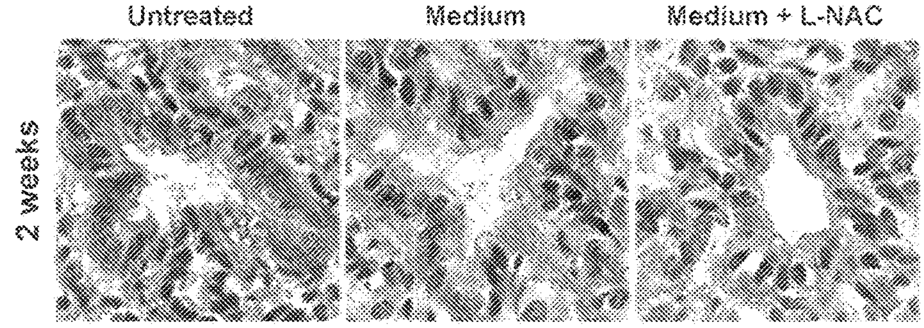
FIGS. 2A-2D are images of exemplary slices of extrahepatic bile ducts (EHBDs) dissected from Mdr2$^{-/-}$ mice and histologically stained with H&E, immune-stained and/or DAPI stained.
Figure 2B:
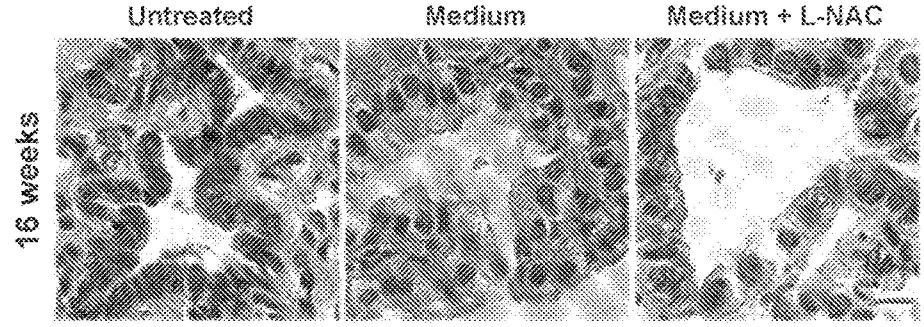
Figure 2C:
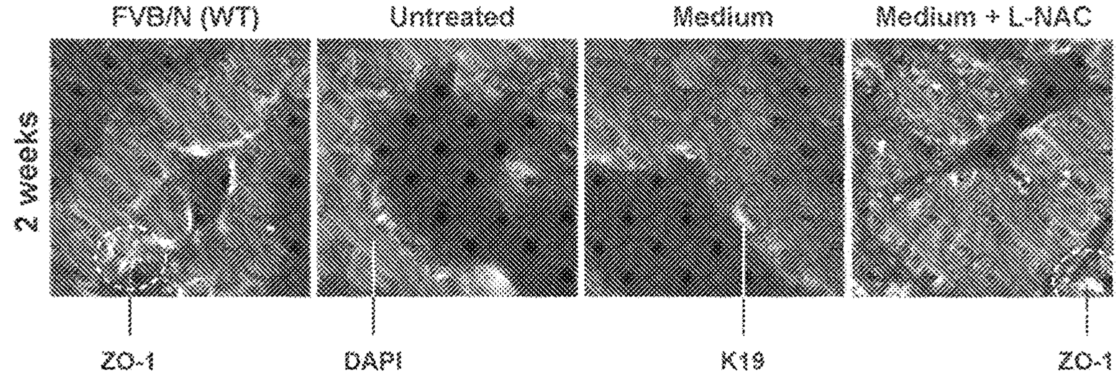
Figure 2D:
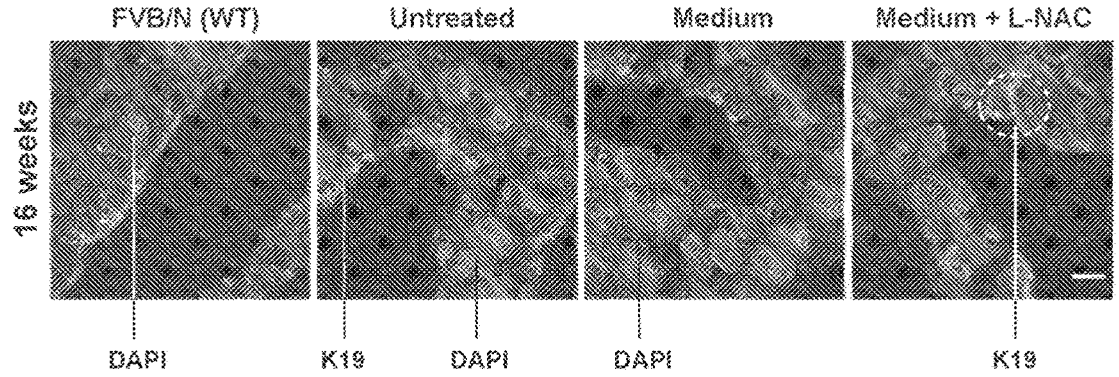

As shown in FIG. 2A, histological damage, including coarse chromatin and nuclear crowding, in 2-week old $Mdr2^{-/-}$ EHBDs were improved with L-NAC treatment. Similar improvement in chromatin quality was observed in EHBDs from 16-week-old $Mdr2^{-/-}$ mouse treated with L-NAC as compared to age-matched untreated mutants, although the effect was subtler (FIG. 2B). Indeed, treatment with L-NAC and fresh BEC media for 24 hours, improved duct architecture with a more normal appearing columnar epithelium. L-NAC also restored expression of the tight junction protein ZO-1, which was lost already in 2-week old $Mdr2^{-/-}$ EHBDs (FIG. 2C). However, restoration of the apical tight junction ZO-1 was not seen in the more severely affected 16-week old $Mdr2^{-/-}$ mouse after 24 hours of treatment (FIG. 2D).

It is shown herein that $Mdr2^{-/-}$ mice EHBD explants that were treated locally with L-NAC for 24 hours showed substantial morphological recovery. Moreover, L-NAC-treated EHBDs that were dissected from 2-week-old mice restored apical tight junction expression. This demonstrates better tissue reorganization at an earlier stage of injury. Thought there was a significant histological improvement with L-NAC treatment at 16 weeks of age, a poor ZO-1 restoration either demonstrates better tissue regeneration capability at an earlier stage of injury, or that at later stages of injury, a longer duration of therapy may be required to completely restore cholangiocyte tight junctions.

Example 3

In Vivo Treatment of $Mdr2^{-/-}$ Mice with L-NAC

The liver repair effect in $Mdr2^{-/-}$ mice treated with L-NAC was assessed. For a test group of 4-month old $Mdr2^{-/-}$ mice, the drinking water were supplemented with 30 gr/L of L-NAC for a period of 3 weeks, and replaced 3 times a week. The control group comprised $Mdr2^{-/-}$ mice which received drinking water without L-NAC. Each group contained 7 mice. Livers of the treated mice were dissected, sectioned and stained with H&E and Sirius Red. The histologic staining images are presented in FIGS. 3A-3B.

Figure 3A:
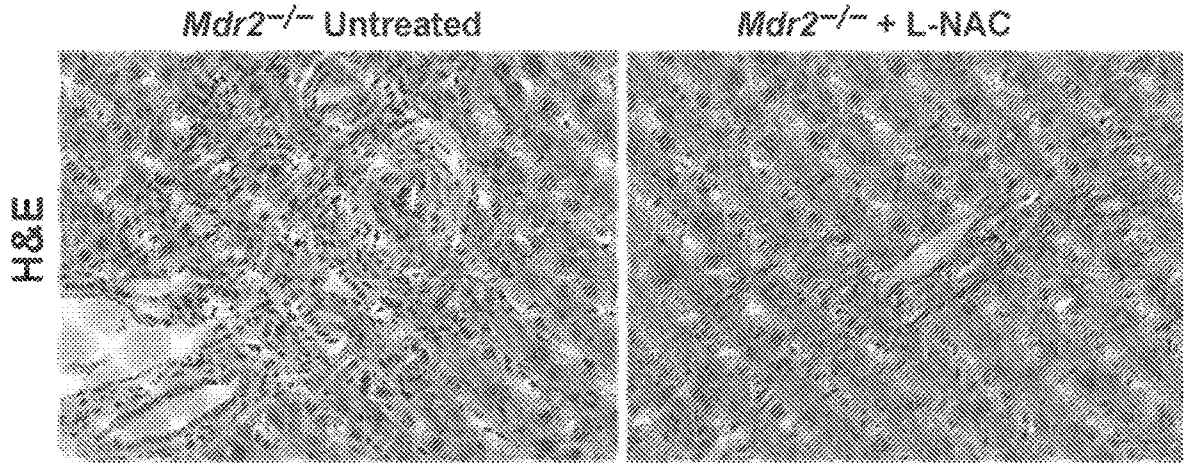
FIGS. 3A-3B are exemplary images of slices of liver dissected from Mdr2$^{-/-}$ mice and histologically stained with H&E (3A) or Sirius Red (3B). Scale bar=100 μM.
Figure 3B:
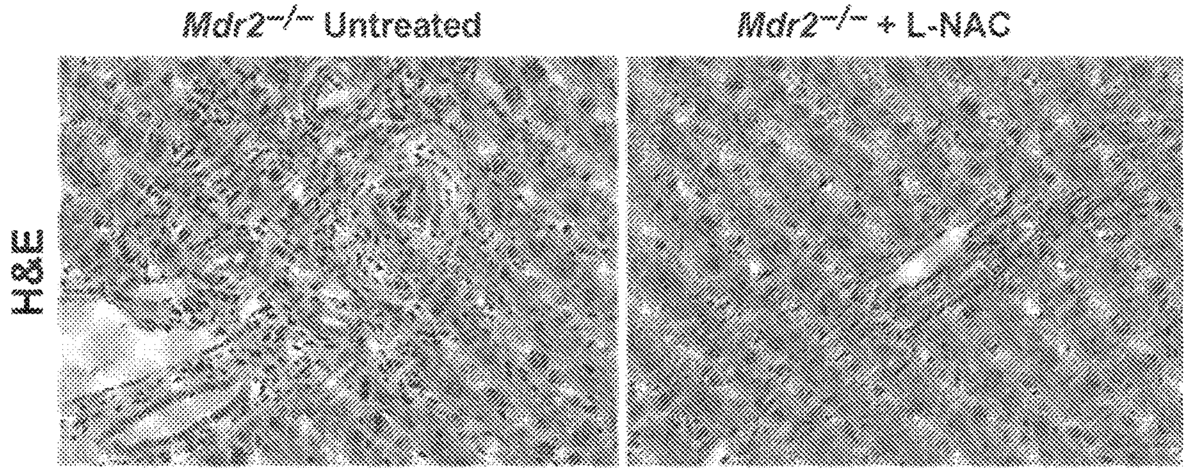

As seen in FIG. 3A, livers from $Mdr2^{-/-}$ mice treated with L-NAC demonstrated reduced portal fibrosis, and reduction in inflammatory cell infiltration around the portal areas. In addition, Sirius Red staining revealed a reduction in liver fibrosis in a $Mdr2^{-/-}$ mouse treated with L-NAC compared to untreated mouse (FIG. 3B).

Example 4

In-Vivo Systemic Treatment of Injured Extrahepatic Bile Ducts with L-NAC

The ability of L-NAC systemic treatment to prevent or ameliorate EHBDs damage is assessed in-vivo.

For this purpose, L-NAC (4 g/kg body weight per day) is added to the drinking water of the $Mdr2^{-/-}$ mice and wild type mice (control), based on an established protocol (Monti et al., *Hum Mol Genet.* 24(19):5570-80, 2015). The EHBDs are dissected when mice reach different ages. Two additional control groups, each comprising wild type and $Mdr2^{-/-}$ mice are tested: the first one is not supplemented with L-NAC, and the second one receives D-NAC in the drinking water. The D isomer does not increase GSH. These controls serve for determining whether adding L-NAC systemically ameliorates or slows down the EHBDs injury. Extrahepatic bile ducts patency is then assessed by H&E staining and immune-stained for K19 as described in Materials and Methods.

For each of the above test and control mice groups, GSH in the liver and EHBDs is measured using a glutathione assay kit (Sigma-Aldrich) in order to determine whether L-NAC administration via drinking water affects GSH levels in the EHBDs and the liver.

Example 5

Ex-Vivo, Local Treatment of Human Extrahepatic Bile Ducts with L-NAC

In order to correlate the findings obtained with mice to the human disease, human EHBDs with duct damage pathology dissected, for example, from patients afflicted with PSC, biliary atresia or other cholangiopathies, and normal EHBDs (e.g., from liver transplant patients having other metabolic diseases), are treated in a Culture Incubator (at 37° C., in 95% $O_2$ and 5% $CO_2$) with L-NAC for 24 hours. The human EHBDs are then assessed for morphology modifications such as improvement in ducts lumens.

What is claimed is:

1. A method of treating a damaged bile duct in a subject having a damaged bile duct, the method comprising administering to the subject a pharmaceutically effective amount of one or more active agents which promote elevation of glutathione (GSH) levels or restoration of normal GSH levels, and/or maintenance of normal GSH levels in the biliary duct, wherein elevation, restoration, or maintenance of GSH levels occurs in biliary epithelial cells (BECs), thereby treating the damaged bile duct in the subject, wherein the damaged bile duct is other than a bile duct having damage due to ligation.

2. The method of claim 1, wherein treating a damaged bile duct is preventing or inhibiting further damage in the damaged bile duct.

3. The method of claim 1, wherein said administering step comprises locally administering said one or more active agents to the damaged bile duct.

4. A method for treatment of biliary duct damage in a subject having a damaged biliary duct, the method comprising locally administering to the damaged biliary duct of the subject a pharmaceutically effective amount of one or more active agents which promote at least one of: elevation of glutathione (GSH) levels, restoration of normal GSH levels, or maintenance of normal GSH levels in the biliary ducts, thereby treating the damaged biliary duct.

5. The method of claim 4, wherein restoration and/or maintenance of normal GSH levels is at least one of: elevating decreased GSH level, inhibiting decease in normal GSH level, or preventing decease in normal GSH level in biliary epithelial cells (BECs).

6. The method of claim 1, wherein elevating GSH levels is increasing GSH concentration above normal levels.

7. The method of claim 1, wherein the active agent is at least one of N-acetyl-L-cysteine (L-NAC), a L-NAC derivative, alpha lipoic acid, calcitriol, S-adenosylmethionine (SAMe) or sulforaphane.

8. The method of claim 7, wherein the active agent is L-NAC.

9. The method of claim 1, wherein the damaged bile duct is extrahepatic bile duct (EHBD) and/or intrahepatic bile duct (IHBD).

10. The method of claim 1, wherein the subject is one whose bile duct is damaged by a cholangiopathy and/or cholestasis.

11. The method of claim 10, wherein:

(i) the cholangiopathy is at least one of: immune-mediated cholangiopathy, infectious cholangiopathy, genetic cholangiopathy, ischemic cholangiopathy, or drug- or toxin-induced cholangiopathy; and/or (ii) cholestasis is caused by at least one of: a cholangiopathy, cholangitis, viral, bacterial, and/or parasitic infection, oxidative stress, immunological assaults, biliary epithelial injuries, bile duct sclerosis, or anastomosis strictures post liver transplant.

12. The method of claim 11, wherein the cholangiopathy is primary biliary cholangitis (PBC), primary sclerosing cholangitis (PSC), IgG4-related sclerosing cholangitis or biliary atresia (BA), and the biliary epithelial injury is basic injury of biliary epithelial cells (BECs) selected from necrosis, apoptosis, or hyperplasia.

13. The method of claim 1, wherein the active agent which promotes increase in GSH production, inhibits GSH degradation or maintains GSH normal levels is locally delivered to the biliary duct lumen by one or more means that provide one of: immediate local release of the active agent, or sustained local release thereof.

14. The method of claim 13, wherein the delivery means is at least one of a stent, a biliary implant, gel, or beads.

15. The method of claim 14, wherein the stent is a biodegradable biliary stent.

16. The method of claim 15, wherein the biodegradable biliary stent provides sustained release of NAC and/or a derivative thereof.

17. A method of treating a damaged bile duct in a subject having a damaged bile duct, the method comprising administering to the subject a pharmaceutically effective amount of one or more active agents which promote elevation of glutathione (GSH) levels or restoration of normal GSH levels, and/or maintenance of normal GSH levels in the biliary duct, wherein elevation, restoration, or maintenance of GSH levels occurs in biliary epithelial cells (BECs), thereby treating the damaged bile duct in the subject, wherein the damaged bile duct is a bile duct whose damage is caused by a cholangiopathy and/or cholestasis.

18. The method of claim 17, wherein:

(i) the cholangiopathy is at least one of: immune-mediated cholangiopathy, infectious cholangiopathy, genetic cholangiopathy, ischemic cholangiopathy, or drug- or toxin-induced cholangiopathy; and/or (ii) cholestasis is caused by at least one of: a cholangiopathy, cholangitis, viral, bacterial, and/or parasitic infection, oxidative stress, immunological assaults, biliary epithelial injuries, bile duct sclerosis, or anastomosis strictures post liver transplant.

19. The method of claim 18, wherein the cholangiopathy is primary biliary cholangitis (PBC), primary sclerosing cholangitis (PSC), IgG4-related sclerosing cholangitis or biliary atresia (BA), and the biliary epithelial injury is basic injury of biliary epithelial cells (BECs) selected from necrosis, apoptosis, or hyperplasia.

20. The method of claim 17, wherein said administering step comprises locally administering said one or more active agents to the damaged bile duct.

* * * * *